US010864302B2

(12) United States Patent
Lee et al.

(10) Patent No.: US 10,864,302 B2
(45) Date of Patent: Dec. 15, 2020

(54) ADHESION PREVENTION AGENT COMPRISING INJECTABLE THERMOSENSITIVE WOOD BASED-OXIDIZED CELLULOSE NANOFIBER

(71) Applicants: Soonchunhyang University Industry Academy Cooperation Foundation, Asan-si (KR); National Institute of Forest Science, Seoul (KR)

(72) Inventors: Byong Taek Lee, Cheonan-si (KR); Sun-Young Lee, Seoul (KR); Tamanna Sultana, Cheonan-si (KR); Celine Abueva, Cheonan-si (KR)

(73) Assignees: SOONCHUNHYANG UNIVERSITY INDUSTRY ACADEMY COOPERATION FOUNDATION, Asan-si (KR); NATIONAL INSTITUTE OF FOREST SCIENCE, Seoul (KR)

( * ) Notice: Subject to any disclaimer, the term of this patent is extended or adjusted under 35 U.S.C. 154(b) by 18 days.

(21) Appl. No.: 15/987,019

(22) Filed: May 23, 2018

(65) Prior Publication Data
US 2019/0015564 A1 Jan. 17, 2019

(30) Foreign Application Priority Data

Jul. 14, 2017 (KR) .......................... 10-2017-0089348

(51) Int. Cl.
| | | |
|---|---|---|
| *A61L 31/14* | (2006.01) | |
| *A61L 31/12* | (2006.01) | |
| *A61L 31/04* | (2006.01) | |
| *A61L 31/06* | (2006.01) | |

(52) U.S. Cl.
CPC .......... *A61L 31/041* (2013.01); *A61L 31/042* (2013.01); *A61L 31/06* (2013.01); *A61L 31/125* (2013.01); *A61L 31/14* (2013.01); *A61L 31/145* (2013.01); *A61L 31/148* (2013.01); *A61L 2400/06* (2013.01); *A61L 2400/12* (2013.01)

(58) Field of Classification Search
None
See application file for complete search history.

(56) References Cited

U.S. PATENT DOCUMENTS

| | | | | | |
|---|---|---|---|---|---|
| 5,013,769 | A | * | 5/1991 | Murray | ............... A61L 26/0052 424/484 |
| 8,936,784 | B2 | * | 1/2015 | Shalaby | ................. A61K 38/36 424/93.72 |

FOREIGN PATENT DOCUMENTS

KR  10-2010-0132878  12/2010

OTHER PUBLICATIONS

Zhang et al.; "Thermosensitive methyl celllulose-based injectable hydrogel for post-operative anti-adhesion," 2014, Elsevier; Carbohydrate Polymers, vol. 101, pp. 171-178. (Year: 2014).*
Tamanna Sultana et al.; "Evaluation of thermo-responsive injectable hydrogel containing oxidized cellulose nanofibre for post surgical adhesion prevention", 2016 Korea Material Society Fall Conference Korea-Japan Materials Engineering Symposium dated on Nov. 15, 2016, pp. 1-3, as provided. (Year: 2016).*
Karim et al.; "Nanocellulose as Novel Supportive Functional Material for Growth and Development of Cells," 2015, Cell & Development Biology, vol. 4, No. 2, article 154, pp. 1-7. (Year: 2015).*
Wei et al.; Thermo-responsive and compression properties of Tempo-oxidized cellulose nanofiber-modified PNIPAnn hydrogels, Apr. 5, 2016; Elsevier, Carbohydrate Polymers, vol. 147, pp. 201-207. (Year: 2016).*
Tamanna Sultana et al., "Evaluation of thermo-responsive injectable hydrogel containing oxidized cellulose nanofibre for post surgical adhesion prevention", 2016 Korea Material Society Fall Conference Korea-Japan Materials Engineering Symposium dated on Nov. 15, 2016, pp. 1-3, as provided.

* cited by examiner

*Primary Examiner* — Devang K Thakor
*Assistant Examiner* — Ivan A Greene
(74) *Attorney, Agent, or Firm* — Lex IP Meister, PLLC

(57) ABSTRACT

The present invention provides a method for preparing an injectable thermosensitive hydrogel for preventing adhesion including mixing methyl cellulose, polyethylene glycol, oxidized cellulose nanofibers and carboxymethyl cellulose. The injectable thermosensitive hydrogel for preventing adhesion is a sol at a low temperature and induces rapid gelation upon in vivo implantation due to thermosensitivity. In addition, the hydrogel can be rapidly changed into physical hydrogel without separate additives or chemical reaction during in vivo condition. In addition, the injectable thermosensitive hydrogel for preventing adhesion exhibits excellent biodegradability and biocompatibility, has no cytotoxicity, inhibits in vitro migration of rat bone marrow mesenchymal stem cells (rBMSCs), and exhibits anti-adhesion efficacy in a rat model of sidewall defect-cecum abrasion in vivo, thus being useful as an effective anti-adhesive agent.

6 Claims, 13 Drawing Sheets

ADHESION PREVENTION AGENT COMPRISING INJECTABLE THERMOSENSITIVE WOOD BASED-OXIDIZED CELLULOSE NANOFIBER

BACKGROUND OF THE INVENTION

Field of the Invention

The present invention relates to a method for preparing an injectable thermosensitive hydrogel for preventing adhesion.

Description of the Related Art

Currently, there are no definitive strategies to prevent the formation of peritoneal adhesions. One of the most widely used anti-adhesion strategies is the application of physical barriers which can separate and isolate wounded tissue after surgery. At present, several anti-adhesion barriers have been approved by the FDA, USA.

The anti-adhesive should be nontoxic, biodegradable, and effective in the target area for at least 5 days. The thermosensitive injectable hydrogels may be ideal agents for postoperative adhesion prevention because they are free flowing solutions before administration and can form gels under physiological conditions to separate the wound surface from the surrounding tissue or organs with minimal invasiveness.

Methyl cellulose or a derivative thereof is known to prevent adhesion and sodium carboxymethyl cellulose (SCMC) is used as a representative material thereof.

In addition, polyethylene glycol (PEG), which is a water-soluble polymer, has been introduced into animal tests together with an anti-adhesion membrane made of carboxymethyl cellulose (CMC) which is a bioresorbable material well-known as a commercial anti-adhesive agent.

Methyl cellulose (MC) has inverse thermogelling. As temperature increases, hydrogen bonds between polymers and neighboring solvent are broken and hydrophobic junctions are formed to create a gel. When polyethylene glycol (PEG) is incorporated into methyl cellulose (MC) gel, polyethylene glycol (PEG) diffuses onto the surface to prevent adhesion.

However, this polymer solution fails to exhibit the desired adhesion prevention effects since it is absorbed excessively faster.

Accordingly, as a result of repeated efforts to produce anti-adhesive agents with better functions while solving problems of the anti-adhesive agents using carboxymethyl cellulose (CMC), methyl cellulose (MC) and polyethylene glycol (PEG) or carboxymethyl cellulose (CMC) and polyethylene glycol (PEG), the present inventors identified that adhesion prevention effects change depending on mix ratios of methyl cellulose, polyethylene glycol, oxide cellulose nanofibers and carboxymethyl cellulose, and produced anti-adhesive agents with optimal effects, thus completing the present invention.

PRIOR ART

Patent Document (Patent Document) Korean Patent Laid-open No. 10-2010-0132878

SUMMARY OF THE INVENTION

Therefore, the present invention has been made in view of the above problems, and it is one object of the present invention to provide a method for preparing an injectable thermosensitive hydrogel for preventing adhesion including preparing an injectable thermosensitive hydrogel for preventing adhesion.

It is another object of the present invention to provide an injectable thermosensitive hydrogel for preventing adhesion prepared by the method.

It is another object of the present invention to provide an injectable thermosensitive anti-adhesive agent including methyl cellulose, polyethylene glycol, oxidized cellulose nanofibers and carboxymethyl cellulose.

The present inventors found that the injectable thermosensitive hydrogel for preventing adhesion prepared by mixing methyl cellulose, polyethylene glycol, oxidized cellulose nanofibers and carboxymethyl cellulose exhibited superior biodegradability and biocompatibility, had no cytotoxicity, inhibited cellular transfer of in vitro rat bone marrow mesenchymal stem cells (rBMSC), and exhibited an anti-adhesion efficacy in a rat sidewall defect-cecum abrasion model in vivo.

In accordance with the present invention, the above and other objects can be accomplished by the provision of a method for preparing an injectable thermosensitive hydrogel for preventing adhesion including mixing methyl cellulose, polyethylene glycol, oxidized cellulose nanofibers and carboxymethyl cellulose, adding water to the resulting mixture, followed by heating, to prepare a mix solution, and cooling and stirring the solution to prepare an injectable thermosensitive hydrogel for preventing adhesion.

The method for preparing an injectable thermosensitive hydrogel for preventing adhesion according to the present invention includes mixing methyl cellulose, polyethylene glycol, oxidized cellulose nanofibers and carboxymethyl cellulose.

In the present invention, a novel injectable thermosensitive hydrogel is prepared according to the schematic diagram shown in FIG. 1.

First, samples of methyl cellulose (MC), polyethylene glycol (PEG), oxidized cellulose nanofibers (OCN) and carboxymethyl cellulose (CMC) were weighed, placed in a glass bottle containing a stirrer and dry-mixed properly.

The methyl cellulose, polyethylene glycol, oxidized cellulose nanofibers and carboxymethyl cellulose may be mixed in a weight ratio of 1 to 3:1:0 to 1:0 to 1, specifically in a weight ratio of 2:1:0.2:0.8.

In an embodiment of the present invention, methyl cellulose, polyethylene glycol, oxidized cellulose nanofibers and carboxymethyl cellulose are mixed to prepare CMC 1 having a weight ratio of MC:PEG:CMC=2:1:1, OCN 0.2 having a weight ratio of MC:PEG:OCN:CMC=2:1:0.2:0.8, OCN 0.5 having a weight ratio of MC:PEG:OCN:CMC=2:1:0.5:0.5, OCN 0.8 having a weight ratio of MC:PEG:OCN:CMC=2:1:0.8:0.2, and OCN 1 having a weight ratio of MC:PEG:OCN=2:1:1.

The method for preparing an injectable thermosensitive hydrogel for preventing adhesion according to the present invention includes adding water to the resulting mixture and heating to prepare a mix solution.

In an embodiment of the present invention, after mixing, water is added to the glass bottle and the glass bottle is placed in a water bath (at temperature of 85° C.), followed by heating. The resulting powder was mixed with vigorous stirring to prepare mix solutions in various weight ratios.

The method for preparing an injectable thermosensitive hydrogel for preventing adhesion according to the present invention includes cooling and stirring the mix solution to prepare an injectable thermosensitive hydrogel for preventing adhesion.

The heating suspension (mix solution) was placed in an ice box (0° C.), allowed to be cooled and stirred homogeneously until formation of a transparent solution to prepare an injectable thermosensitive hydrogel for preventing adhesion. The prepared solution was stored at 4° C.

In the present invention, the oxidized cellulose nanofibers may be derived from wood materials. Nanocellulose is a biomaterial candidate. Nanocellulose may be used in regenerative medicine such as scaffolds, for example, tissue engineered meniscus, blood vessel, ligaments and tendon replacements, and in wound healing applications. This is due to considerable physical properties and specific surface chemistry of nanocellulose as well as excellent biological properties such as biodegradability, biocompatibility and low toxicity thereof.

In order to produce cellulose nanofibers, wood cellulose fibers need to be isolated. It is difficult to isolate cellulose fibers at a high efficiency because they have strong fiber-fiber bonds, but uniform cellulose nanofibers can be obtained by oxidizing with the functional catalyst, 2,2,6,6-tetramethyl-piperidin-1-oxy (TEMPO). The oxidized cellulose nanofibers (CNFs) are derived from wood-based biomass and thus have biodegradability. In addition, oxidized cellulose nanofibers (CNFs) are applicable to polymer composite materials, medical engineering materials and membranes, because they have excellent properties such as high crystallinity, excellent heat resistance and superior transparency.

In the present invention, the injectable thermosensitive hydrogel for preventing adhesion is prepared using oxidized cellulose nanofibers obtained by TEMPO-mediated oxidation of nanocellulose. The oxidized cellulose nanofibers (OCNs) have excellent crystallinity and water solubility, providing formation of hydrogels to create a 3D environment allowing for cellular growth and differentiation.

In the present invention, the term "suspension" means a floating system wherein solid fine particles are dispersed in a liquid.

In the present invention, the term "homogeneous" means that, although any part is taken from one substance in a certain state, it has the same physical and chemical properties as another part.

In the present invention, the term "adhesion" means a phenomenon in which the skin, membrane and the like separated from each other are attached to one another. If tissue damage occurs after surgical operation or due to inflammation, foreign matter, hemorrhage, infection, wound, friction, chemical treatment or the like, blood leaks out during the healing process of the wound, resulting in an adhesion phenomenon meaning abnormal attachment to peripheral tissues. These adhesions are particularly frequent after surgical operation. Pelvic adhesion may cause chronic pain, sexual dysfunction or the like, and adhesion due to scar formation after thyroidectomy may reduce side effects such as chest pain and difficulty in swallowing, adhesion by spinal surgery results in severe nerve compression and severe pain, and intrauterine adhesion is known to cause infertility, amenorrhea and addictive abortion.

The injectable thermosensitive hydrogel for preventing adhesion according to the present invention has thermosensitivity of showing a sol-gel transition depending on temperature and is thus gelled in vivo at a body temperature when applied as a biomaterial in vivo.

In addition, the injectable thermosensitive hydrogel for preventing adhesion is a biodegradable material and has thermosensitivity of showing a sol-gel behavior depending on temperature, such that it can be easily injected as a solution into the body and can form a three-dimensional gel within a short time due to body temperature.

In addition, the injectable extracellular matrix-based hydrogel has better strength than conventional thermosensitive polymers having sol-gel behaviors and can thus be utilized in various applications requiring strength such as tissue engineering materials, for example, implant materials and artificial cartilage, and can be practically applied to the human body.

The injectable extracellular matrix-based hydrogel prepared by the method is specifically a gel at 37° C.

In an embodiment of the present invention, the injectable thermosensitive hydrogel for preventing adhesion is a transparent liquid solution at 4° C. and becomes turbid and changes into a solid gel when temperature is elevated to 37° C., which indicates that gelation effectively occurs in vivo at 37° C., the body temperature. In addition, as compared to in situ chemically cross-linked hydrogels, the solution prepared in Example 1 could form hydrogels without separate additives or chemical reactions.

In addition, in an embodiment of the present invention, the weight loss of OCN 0.2 hydrogel gradually increased over time, indicating that OCN 0.2 hydrogel was degraded and could be effectively degraded even after in vivo implantation. In addition, as the content of OCN mixed with the hydrogel decreases, degradability increases. In particular, as the weight reduction of OCN 0.2 hydrogel composed of methyl cellulose, polyethylene glycol, oxidized cellulose nanofibers and carboxymethyl cellulose mixed in a weight ratio of 2:1:0.2:0.8 gradually increases, it shows highest degradability. In vivo degradation experimentation demonstrated that OCN 0.2 hydrogel was degraded over time and was thus biocompatible.

In addition, in an embodiment of the present invention, analysis results of gelation time of hydrogel measured in vitro by a test tube inversion method and in vivo injection show in vivo gel formation was significantly faster compared to in vitro gelation. In particular, gelation of the OCN 0.2 solution started after seconds and almost completed within 3 minutes at physiological temperature.

In addition, in an embodiment of the present invention, as a result of analysis of in vivo degradation and biocompatibility of different hydrogels after in vivo subcutaneous injection, OCN 0.2 showed better degradation over time than other gels containing OCN and thus exhibited excellent biocompatibility.

In addition, in an embodiment of the present invention, there was no great difference in cell viability (%) of rBMSCs depending on concentration of OCN, compared to the control group, but CMC 1 not containing oxidized cellulose nanofibers and consisting of methyl cellulose, polyethylene glycol and carboxymethyl cellulose in a weight ratio of 2:1:1, and OCN 0.2 consisting of methyl cellulose, polyethylene glycol, oxidized cellulose nanofibers and carboxymethyl cellulose in a weight ratio of 2:1:0.2:0.8 exhibited better anti-adhesion properties to rBMSCs. Specifically, regarding migration behaviors of rBMSCs towards gel, OCN 0.2 and OCN 1 showed lower migration at 48 hours, indicating in vitro anti-adhesion efficacy.

In addition, in an embodiment of the present invention, a sidewall defect-cecum abrasion rat model is established and hydrogel is applied to defects. Rats treated with hydrogel OCN 0.2 on day 7 and day 14 prevent adhesion between the defected wall and abraded cecum, and promote the remesothelialization of injured cecum and abdominal wall, which means that there is excellent anti-adhesion effect in vivo.

Accordingly, in vitro and in vivo tests demonstrated that the injectable thermosensitive hydrogel for preventing adhesion according to the present invention exhibits excellent biodegradability, biocompatibility and cell proliferation effects, as well as anti-adhesion efficacy. The present invention provides an injectable thermosensitive hydrogel for preventing adhesion which has an advantage of inducing rapid gelation in vivo owing to thermogelling properties to facilitate regeneration of tissues and is thus injectable in vivo.

In another aspect of the present invention, provided is an injectable thermosensitive hydrogel for preventing adhesion prepared by the method.

In another aspect of the present invention, provided is an injectable thermosensitive anti-adhesive agent including methyl cellulose, polyethylene glycol, oxidized cellulose nanofibers and carboxymethyl cellulose.

As described above, the injectable thermosensitive hydrogel for preventing adhesion effectively prevents adhesion and is thus applicable as an in vivo injectable thermosensitive anti-adhesive agent.

In the present invention, the terms of methyl cellulose, polyethylene glycol, oxidized cellulose nanofibers, carboxymethyl cellulose, injectable and thermosensitive, and description associated with adhesion have been described above.

In the present invention, the methyl cellulose, polyethylene glycol, oxidized cellulose nanofibers and carboxymethyl cellulose may be mixed in a weight ratio of 1 to 3:0.5 to 1.5:0 to 1:0 to 1.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, examples of the present invention will be described with reference to the annexed drawings in detail to such an extent that a person having ordinary knowledge in the art to which the present invention pertains can easily implement the examples. However, the present invention can be realized in various forms and is not limited to the examples described herein.

EXAMPLE 1

Preparation of Injectable Thermosensitive Hydrogel

Figure 1:
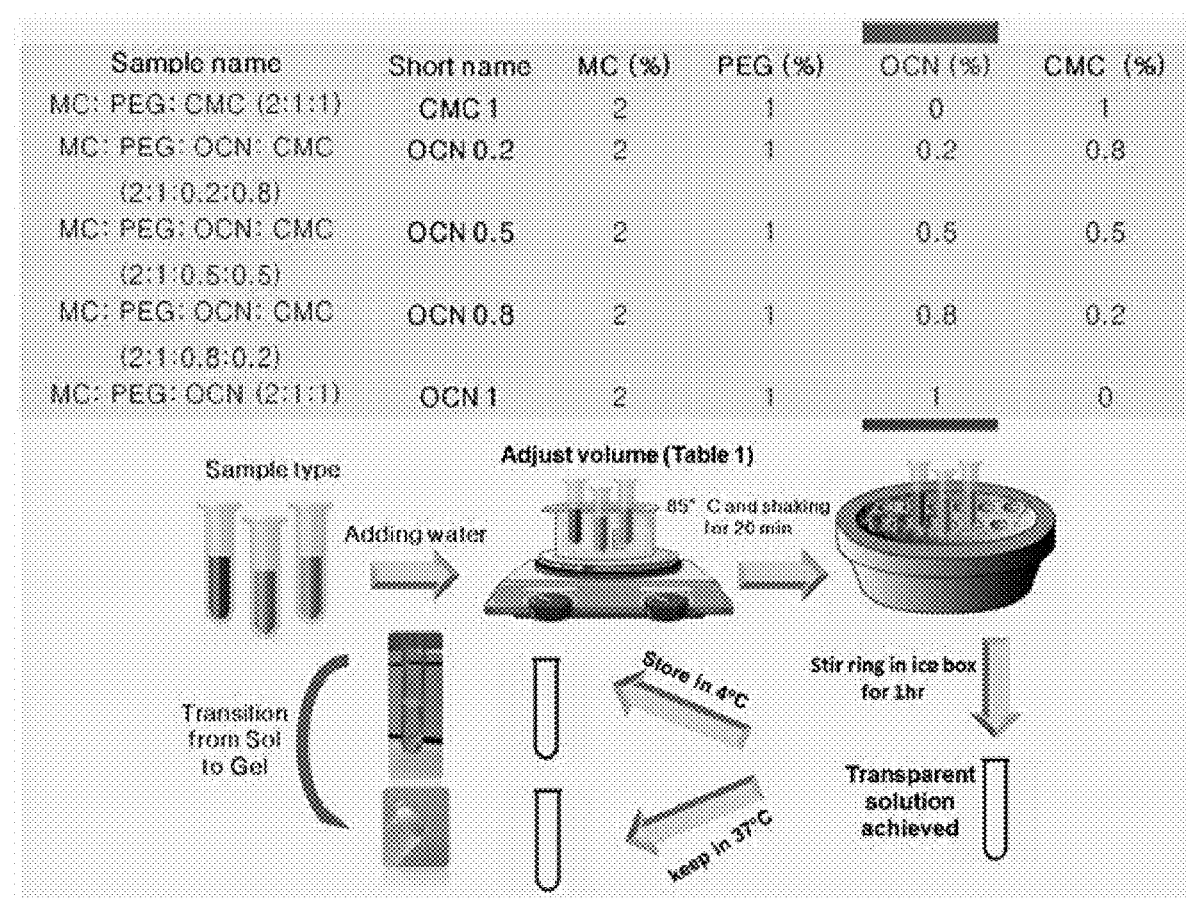
FIG. 1 is a schematic diagram showing a method for preparing various thermosensitive injectable hydrogels having different compositions.

In the present invention, various novel injectable thermosensitive hydrogels are prepared by the following method at different composition ratios according to the schematic diagram shown in FIG. 1.

Chemical samples of methyl cellulose, polyethylene glycol, oxidized cellulose nanofibers and carboxymethyl cellulose shown in Table 1 were weighed, placed in a glass bottle containing a stirrer and dry-mixed properly. Then, water was added thereto and the glass bottle was placed in a water bath (temperature of 85° C.). The mixed powder was vigorously stirred for 20 minutes to prepare a mix solution.

The mixed solution (suspension) was placed in an ice box (0° C.), allowed to be cooled and stirred uniformly until a transparent solution was formed. The prepared solution was stored at 4° C.

Table 1 shows contents of samples for preparing hydrogels according to the present invention.

TABLE 1

| Sample name | Sample composition | MC (%) | PEG (%) | OCN (%) | CMC (%) |
|---|---|---|---|---|---|
| CMC 1 | MC:PEG:CMC (2:1:1) | 2 | 1 | 0 | 1 |
| OCN 0.2 | MC:PEG:OCN:CMC (2:1:0.2:0.8) | 2 | 1 | 0.2 | 0.8 |
| OCN 0.5 | MC:PEG:OCN:CMC (2:1:0.5:0.5) | 2 | 1 | 0.5 | 0.5 |
| OCN 0.8 | MC:PEG:OCN:CMC (2:1:0.8:0.2) | 2 | 1 | 0.8 | 0.2 |
| OCN 1 | MC:PEG:OCN (2:1:1) | 2 | 1 | 1 | 0 |

Abbreviations

MC: methyl cellulose, PEG: polyethylene glycol, OCN: oxidized cellulose nanofibers (OCN), CMC: carboxymethyl cellulose (CMC)

The prepared hydrogel was stored in a liquid phase at 4° C. In addition, it could be confirmed that the prepared hydrogel was gelled at 37° C.

EXAMPLE 2

Fourier-Transform Infrared Spectroscopy (FTIR)

The functional groups present in the hydrogel were determined by Fourier-transform spectroscopy using a Nicolet™ Ia10 spectrometer (Thermo Fisher Scientific). OMNIC version 7.3 software was used to plot a graph in the wavelength range of 4,000 to 600 $cm^{-1}$ at a resolution of about 8 $cm^{-1}$.

EXAMPLE 3

Surface Morphology Measurement

Scanning electron microscopy (SEM) using a JSM-6701F microscope (JEOL, Japan) was used to observe morphology of the electrospun mats. Prior to SEM observation, lyophilized hydrogel and oxidized cellulose nanofibers (OCNs) were cut into small sections and mounted to a sample holder, followed by being coated with platinum under a sputter coater (Cressington Scientific Instrument, Watford, UK).

EXAMPLE 4

Observation of Sol-Gel Transition

The sol-gel phase transition of gel was roughly estimated by the tube-inversion approach. Briefly, 0.5 mL of a solution was added to a test tube and stored at 4° C. for 1 hour, and then the tube was incubated at 37° C. for a certain time and gelation time was measured using a stopwatch. The sample was determined as a "gel" when flow could not be observed by the naked eye within 30 seconds when inverting the tube.

EXAMPLE 5

Rheological Measurement

Using a Brookfield viscometer (Brookfield Instruments, Middleboro, Mass.), the viscosity of each sample was determined at different rpm (0.3, 0.5, 1, 2.5, 5, 10, 20, 30, 50 and 100) under two different temperature conditions (4° C. and 25° C.)

EXAMPLE 6

In Vitro Degradation of Hydrogel

In vitro degradation of hydrogel was monitored as a function of weight loss over time under simulated physiological conditions. 0.5 mL of a solution was injected into a petri dish and incubated at 37° C. for 30 minutes to complete gelation. Then, 5 mL of phosphate buffered saline (PBS) (pH 7.4) was added and changed weekly. pH change was measured with a pH meter before the medium was replaced with fresh one. At predetermined time points, the gels were taken out, lyophilized and weighed (Wt). The weight loss percentage ($\Delta W$ %) at each time interval was calculated using the following equation, wherein W0 is the initial weight of each sample.

$$(\Delta W\%) = (1 - Wt/W0) \times 100$$

EXAMPLE 7

RBMSC Culture

Rat bone marrow mesenchymal stem cells (RBMSCs) were isolated and cultured in $\alpha$-MEM that contained 10% FBS and 1% PS (penicillin 100 U/ml, streptomycin 100 U/ml). After third passage culture, cells were seeded on hydrogel while replacing the media every 2 days.

EXAMPLE 8

Cell Viability and Metabolic Activity (WST Assay)

Approximately $1 \times 10^4$ cells/mL of cells were seeded on the hydrogel in 48-well plates and the plates were kept in a $CO_2$ incubator for 1, 3 and 5 days. The cells were treated with a 1:10 ratio of EZ-CYTOX for cell viability assay to each sampling day. After incubation at 37° C. for 2 hours, absorbance of an orange colored formazan solution was measured at a wavelength of 450 nm using an ELISA reader (EL, 312, Biokinetics reader, Bio-Tek instruments). In addition, OD value indicated the number of viable cells.

EXAMPLE 9

Cell Proliferation and Migration rBMSCs were seeded at a density of $1 \times 10^4$ cells/mL on 24-well culture plates and allowed to grow confluent with proper adhesion and spreading. Scratch of the monolayer of cells was created using a 1,000 µL pipette tip. After scratching, removal of debris and smoothing of the edge of the scratch were done by washing the cells once with 1 ml of the growth medium and then replaced with 5 ml of extract medium of each gel sample and culture medium was used for control. Degree of proliferation was checked at various time points (0, 12, 24 and 48 hours). To check migration, at first, medium was removed and then gel was applied to one side of the scratch and kept in an incubator to allow formation of a solid gel. After that culture medium was applied over the gel, the plates were incubated in a $CO_2$ incubator to check migration behaviors towards gel at 1 and 3 days. Cell images were taken at respective time points with a digital camera connected to a phase-contrast Olympus microscope (BX51, 10× objective). The same visual field was marked and used throughout the experiment. The medium was replaced every two days.

EXAMPLE 10

In Vivo Degradation and Biocompatibility of Hydrogel 0.5 ml of gel was subcutaneously injected into the back of rats by a syringe with a 22-gauge needle. After administration for 0, 7 and 14 days, rats were sacrificed, and the injection sites were opened to observe the state and amount of hydrogel. The gel was rapidly formed after administration. The remaining gels in the rat were taken out using forceps and scissors for analysis. The tissue surrounding the implants was removed, fixed in 4% paraformaldehyde, embedded in paraffin, sectioned, and stained with hematoxylin and eosin (HE) for further histological examination of tissue responses to the synthesized polymers in rats.

EXAMPLE 11

Animals and Surgical Procedure

The anti-adhesion efficacy of hydrogel was evaluated using a rat cecum abrasion model. 18 male Sprague-Dawley rats (Rattus norvegicus) weighing 200 to 250 g were commercially available and then randomly divided into three experimental groups with three rats in each group: Group A—with tempo-oxidized nanocellulose, Group B—without tempo-oxidized nanocellulose and Group C—control. For general anesthesia, a mixture of isoflurane vapor (Isoflurane USP, Piramal, USA) and supply gas (oxygen) was used for general anesthesia by allowing inhalation to animals. Ventral hair was shaved and their abdomens were sterilized with 70% ethanol, followed by povidone iodine. In brief, using an aseptic technique, a 5 cm long incision was made in the linea alba on the abdominal wall, followed by forming 2×2 cm midline of the abdominal wall, and the surface of the cecum was scraped with a scalpel blade until damage and hemorrhage formation, but not to be perforated. The damaged cecum surface was then covered with injectable gels (2.0× 2.0 cm) (approximately 3 ml). Rats in the control group were only washed with saline solution and not covered with any anti-adhesive material. After the above procedures, the cecum and the small bowel were returned to their original locations. The abdominal incision was closed with sutures. The animals were then given free access to food and water. After a predetermined observation period, incisions were reopened and examined for adhesions by the naked eye. The rats were sacrificed thereafter and the treated section was collected for further analysis (histological analysis).

TEST EXAMPLE 1

FT-IR Analysis of Injectable Thermosensitive Hydrogel

In the present invention, a thermoreversible OCN-containing hydrogel was developed and whether or not the hydrogel could be used as a physical barrier membrane (device) to prevent postsurgical adhesion was evaluated.

Specifically, methyl cellulose (MC), polyethylene glycol (PEG), oxidized cellulose nanofibers (OCNs) and carboxymethyl cellulose (CMC) are mixed to prepare CMC 1 having a weight ratio of MC:PEG:CMC=2:1:1, OCN 0.2 having a weight ratio of MC:PEG:OCN:CMC=2:1:0.2:0.8, OCN 0.5 having a weight ratio of MC:PEG:OCN:CMC=2:1:0.5:0.5, OCN 0.8 having a weight ratio of MC:PEG:OCN:CMC=2:1:0.8:0.2, and OCN 1 having a weight ratio of MC:PEG:OCN=2:1:1.

Figure 2A:
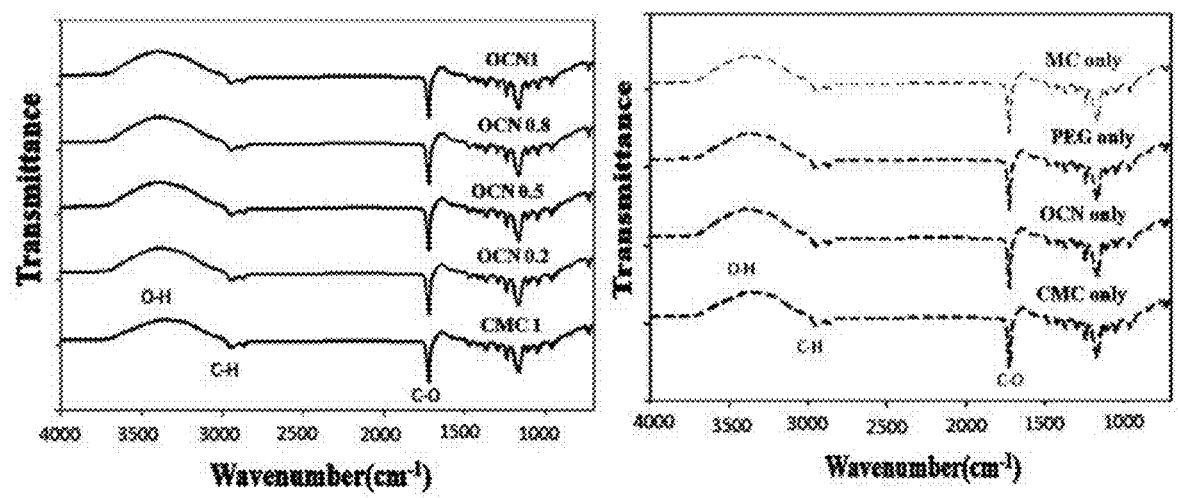
FIG. 2A and FIG. 2B show FT-IR spectra (A) of CMC 1, OCN 0.2, OCN 0.5, OCN 0.8, OCN 1, MC, PEG, OCN and CMC only. The data show different functional groups indicating no formation of chemical bonds. FTIR: Fourier-transform infrared, MC: methyl cellulose, PEG: polyethylene glycol, OCN: oxidized cellulose nanofibers, CMC: carboxymethyl cellulose; and visual observation (B) of thermosensitive behaviors at 4° C. (sol) and at 37° C. (gel)

FIG. 2A shows FT-IR spectrum of only CMC 1, OCN 0.2, OCN 0.5, OCN 0.8, OCN 1, MC, PEG, OCN or CMC, and represents that different functional groups are observed due to no formation of Chemical bonds.

TEST EXAMPLE 2

Identification of Sol-Gel Transition of Injectable Thermosensitive Hydrogel

Figure 2B:
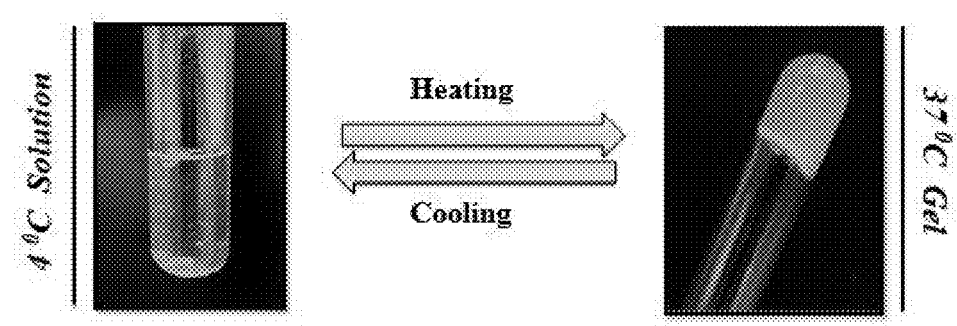

FIG. 2B shows results of observation of thermosensitive behaviors by the naked eye at 4° C. (sol) and at 37° C. (gel). The injectable thermosensitive hydrogel for preventing adhesion was a sol of a transparent liquid state at 4° C. and became turbid and changed into a solid gel when elevating the temperature to 37° C., which indicates that gelation effectively occurs in vivo at 37° C., human body temperature. In addition, as compared to in situ chemically cross-linked hydrogels, the solution prepared in Example 1 could form hydrogels without separate additives or chemical reactions. In general, chemical hydrogels may cause biocompatibility problems, thus being limited in clinical applications due to treatments to induce chemical initiators, inconvenient ultraviolet (UV) irradiation or in vivo chemical reaction. However, the hydrogel solution prepared in Example 1 is free from these problems.

TEST EXAMPLE 3

Viscosity Analysis of Injectable Thermosensitive Hydrogel

Figure 5A:
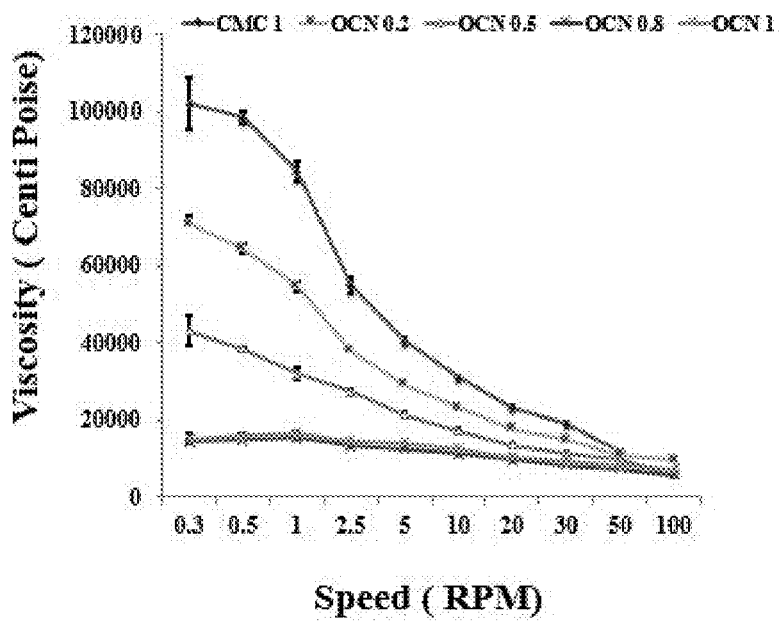
FIG. 5A and FIG. 5B show viscosity of CMC 1, OCN 0.2, OCN 0.5, OCN 0.8 and OCN 1 (A) at a freeze temperature of 4° C. (sol) and (B) at room temperature of 25° C. (gel). Results are expressed as mean±SD.
Figure 5B:
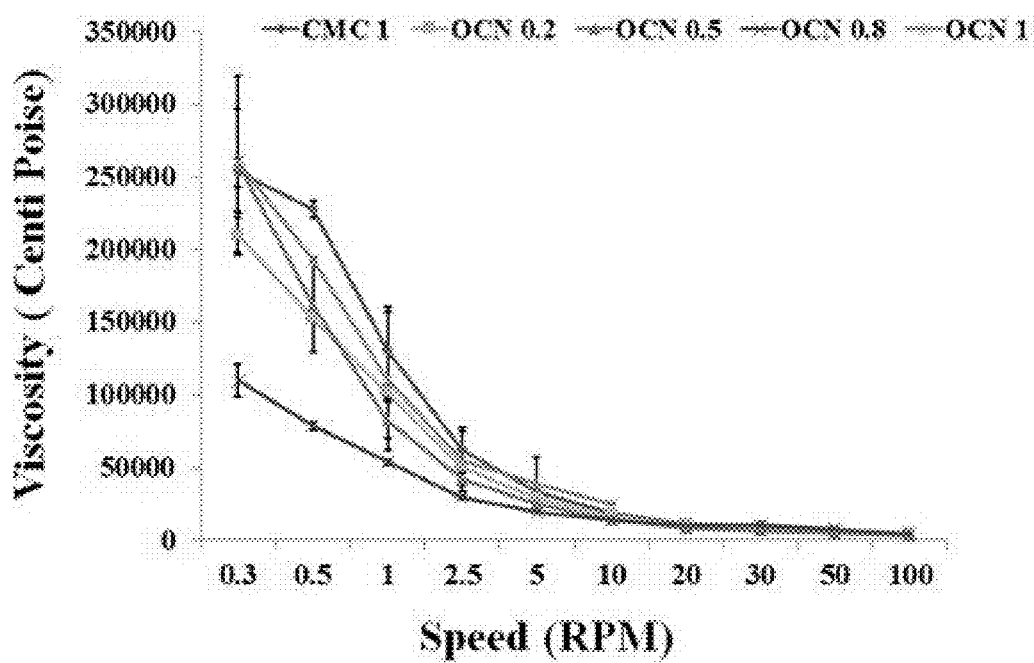

FIG. 5 shows viscosity of CMC 1, OCN 0.2, OCN 0.5, OCN 0.8, and OCN 1 (A) at a freezing temperature of 4° C. (sol) and (B) at room temperature of 25° C. (gel). Results show mean±standard deviation. As content of the oxidized cellulose nanofibers (OCNs) increases, viscosity decreases. In addition, viscosity decreases as rpm increases, viscosity is higher at 25° C. than 4° C. and results of FIG. 5 indicate that the hydrogel was present as a sol at 25° C. or less.

TEST EXAMPLE 4

Morphology and Biodegradability Analysis of Injectable Thermosensitive Hydrogel FIG. 3 shows SEM images of (A), (B) OCN 0.2 gel and (C) oxidized cellulose nanofiber suspension after freeze drying, (D) pH change of the medium with hydrogel degradation and (E) in vitro hydrogel degradation in PBS at 37° C.

Figure 3A:
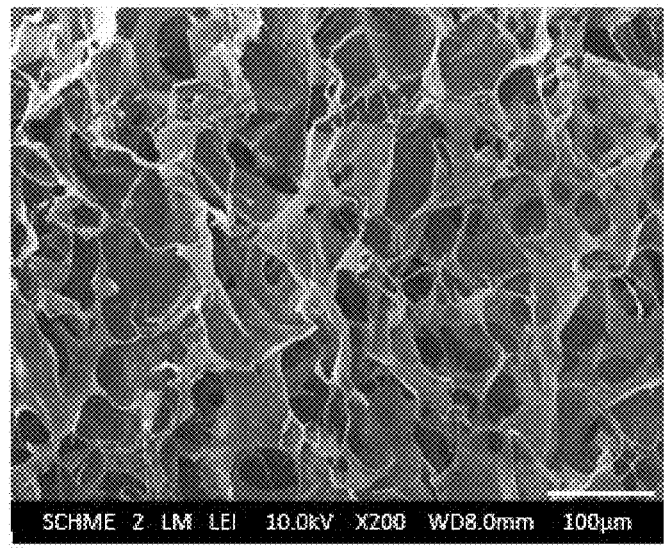
FIG. 3A, FIG. 3B, FIG. 3C, FIG. 3D and FIG. 3E show SEM images of (A), (B) OCN 0.2 gel and (C) oxidized cellulose nanofiber suspension after freeze drying, (D) pH change of the medium with hydrogel degradation, and (E) in vitro hydrogel degradation in PBS at 37° C.
Figure 3B:
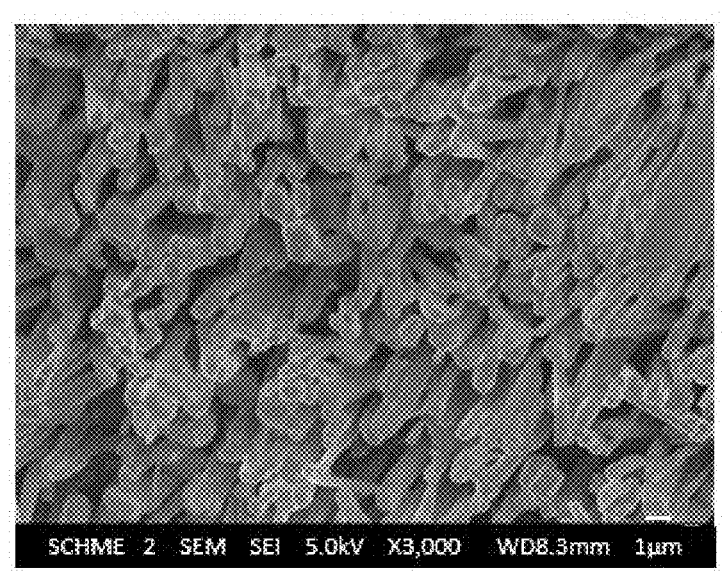
Figure 3C:
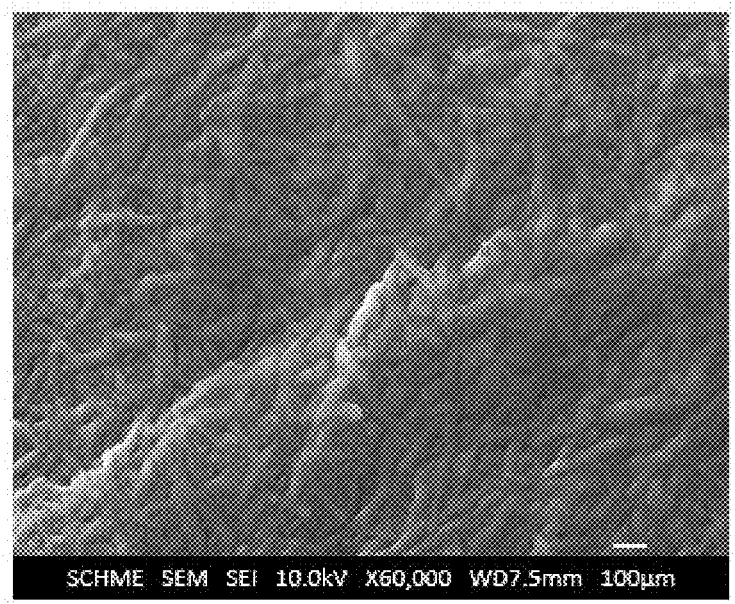

FIG. 3A shows the structure of OCN 0.2 (×200) and FIG. 3B shows the structure of OCN 0.2 (×3000). From these drawings, rough microstructure could superficially be seen and the shape of nanofibers could be seen when magnified at 3000×.

Scanning microscopy results of the hydrogels showed that the OCN 0.2 hydrogel composed of methyl cellulose, polyethylene glycol, oxidized cellulose nanofibers and carboxymethyl cellulose in a weight ratio of 2:1:0.2:0.8 exhibited substantially uniform nanoparticle size and these nanoparticles were uniformly distributed so that the OCN 0.2 hydrogel had the most appropriate hydrogel structure. Based on this structure, the hydrogel could prevent adhesion between cells and serve as an anti-adhesive agent.

Figure 3E:
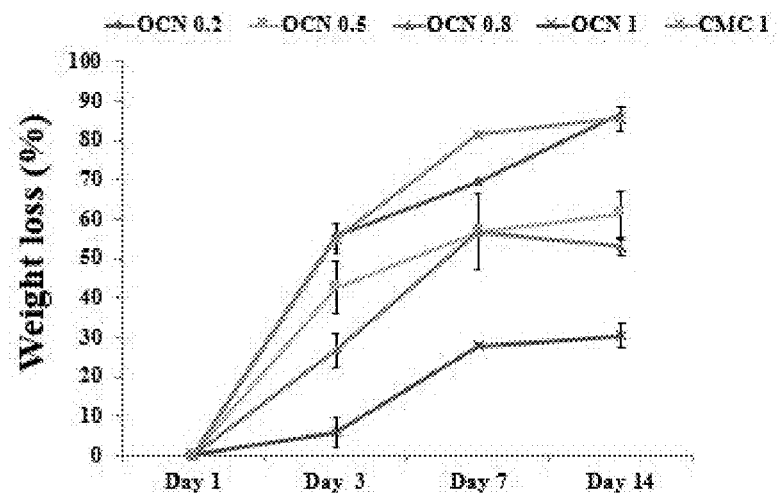
Figure 4:
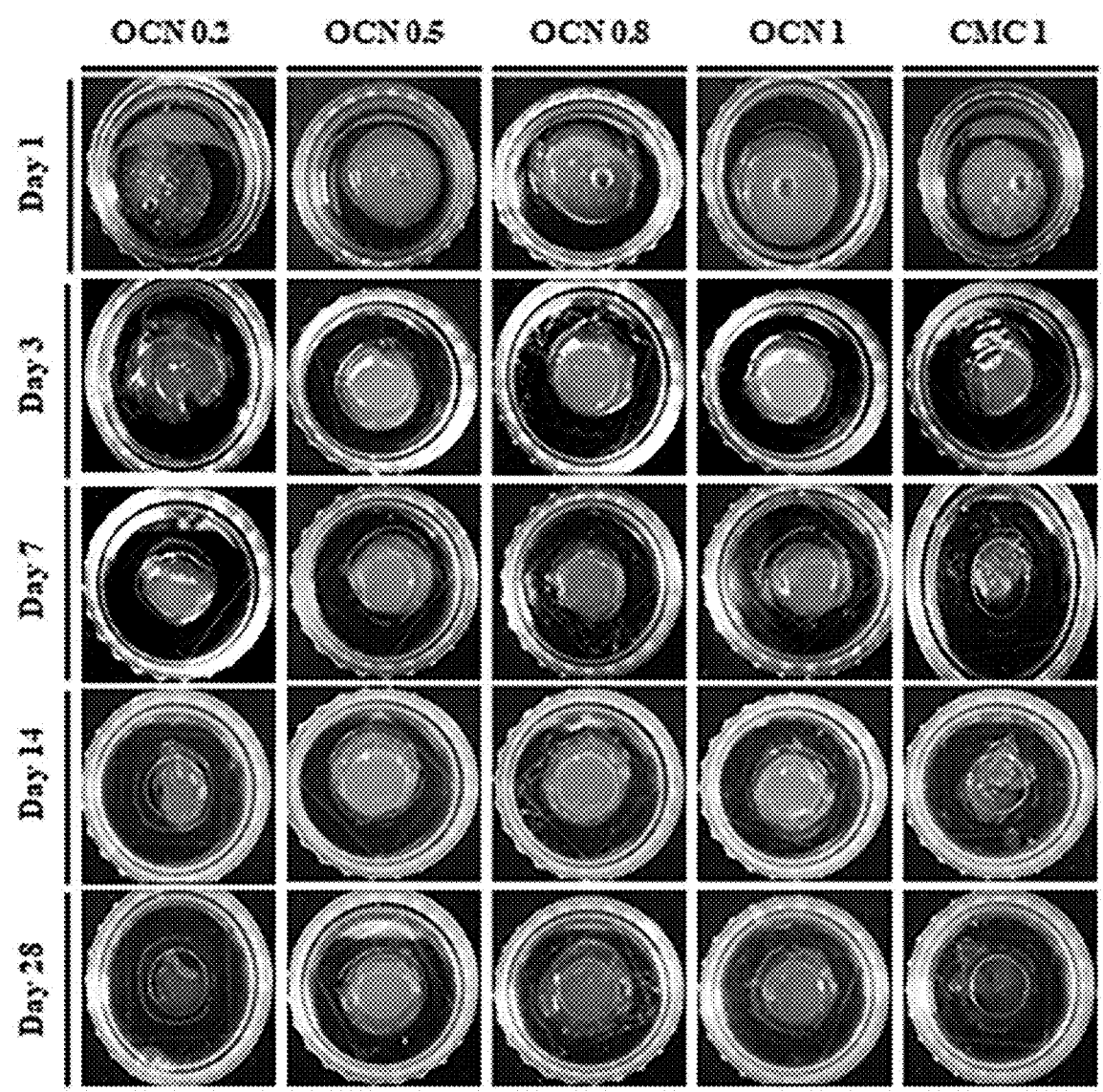
FIG. 4 shows in vitro degradation behaviors of gels in PBS at 37° C. CMC 1 & OCN 0.2 almost degraded within 28 days compared to OCN 0.5, OCN 0.8 and OCN 1.

In vitro degradation experimentation showed the weight loss of OCN 0.2 hydrogel gradually increased over time, indicating that OCN 0.2 hydrogel was degraded and could be effectively degraded even after in vivo implantation. In addition, as the content of OCN mixed with the hydrogel decreases, degradability increases. In particular, as the weight reduction of OCN 0.2 hydrogel composed of methyl cellulose, polyethylene glycol, oxidized cellulose nanofibers and carboxymethyl cellulose mixed in a weight ratio of 2:1:0.2:0.8 gradually increases, it shows the highest degradability (FIGS. 3E and 4).

Figure 3D:
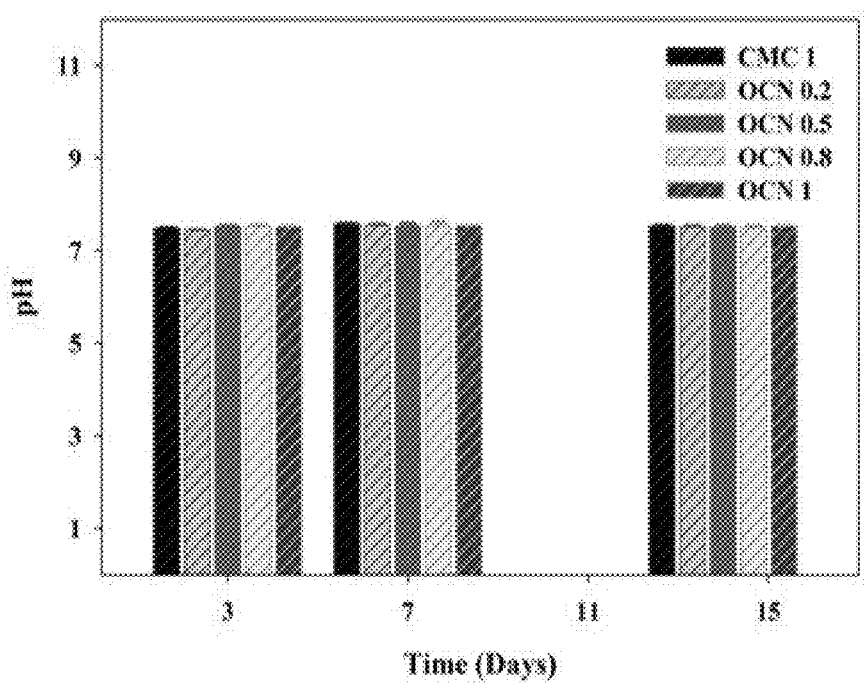

In addition, degradation products had no impact on the pH of the medium (FIG. 3D). In vitro degradation experimentation suggested that OCN 0.2 hydrogel was degraded over time and was thus biocompatible (FIG. 4), which was a satisfactory persistence period for the adhesion prevention application. In addition, the biodegradability and bioabsorbability of the OCN 0.2 hydrogel are advantageous for avoiding secondary surgery and enhancing patient compliance.

TEST EXAMPLE 5

In Vitro Cell Proliferation and Migration Analysis of rBMSCs

Figure 6A:
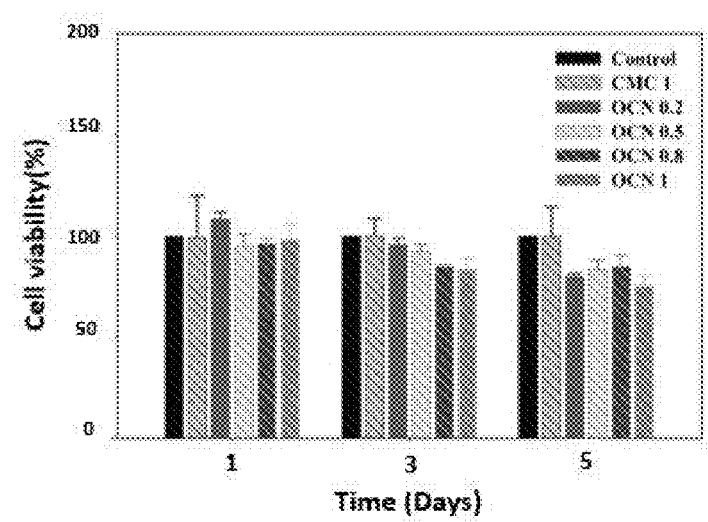
FIG. 6A and FIG. 6B show cell viability (%) of (A) rBMSCs determined by WST Assay. CMC 1 and OCN 0.2 showed better anti-adhesion properties to rBMSCs. (B) rBMSC migration behavior towards gel shows cell migration in lesser extent for samples OCN 0.2 and CMC 1 at 48 hours.

FIG. 6A shows cell viability (%) of rBMSCs determined by WST assay. There was no great difference in cell viability (%) of rBMSCs between the solutions prepared in Example 1, compared to the control group, which indicates that there was no cytotoxicity.

Figure 6B:
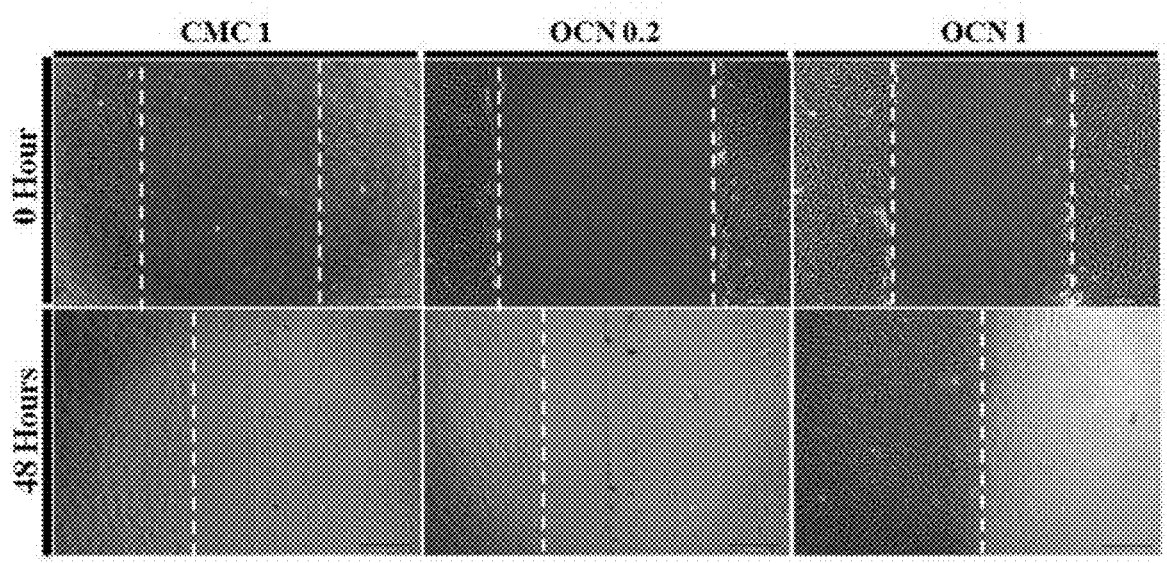

As can be seen from FIG. 6B, CMC 1 and OCN 0.2 composed of methyl cellulose, polyethylene glycol, oxidized cellulose nanofibers and carboxymethyl cellulose mixed in a weight ratio of 2:1:0.2:0.8 exhibited better anti-adhesion property to rBMSCs. Regarding rBMSCs migration behavior towards gel, OCN 0.2 and CMC 1 samples had less cell migration at 48 hours.

Figure 7:
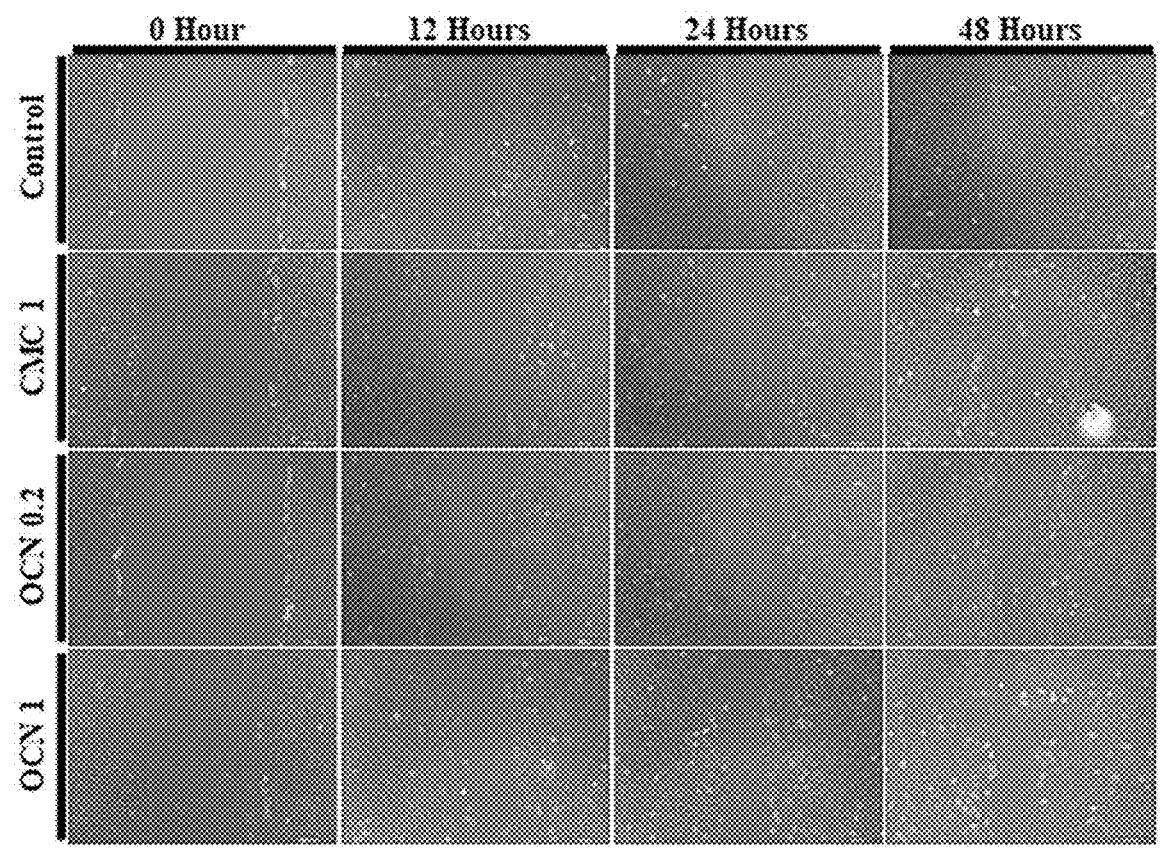
FIG. 7 shows rBMSC cell proliferation (%) determined by migration of cells on extraction media of hydrogels. OCN 0.2 showed lower migration and cell proliferation property towards scratched areas at 48 hours compared to control and OCN 1.

FIG. 7 shows RBMS cells proliferation (%) determined by migration of cells on extraction media of hydrogels. OCN 0.2 showed lower migration and cell proliferation towards scratched areas at 48 hours, compared to control and OCN 1.

In vitro WST analysis showed that the OCN 0.2 hydrogel was non-toxic and promoted proliferation, but had less cell migration towards gels (FIGS. 3D, 3E, and 7). These results suggest that the OCN 0.2 hydrogel is the most suitable as an anti-adhesive agent in the biomedical field.

TEST EXAMPLE 6

Analysis of Gelation Time of Injectable Thermosensitive Hydrogel

The gelation time has an important influence on the application of the injectable hydrogel for adhesion prevention. If the gelation rate is too fast, the injured surfaces cannot be completely covered before gelation, whereas a long gelation time may prolong operation time and increase the risk of infection. For example, Liu et al. prepared chemically crosslinked hyaluronan hydrogels to reduce postoperative abdominal adhesions, while the relatively long gelation time (10-45 minutes) greatly hampered application thereof in clinical practice.

Figure 8:
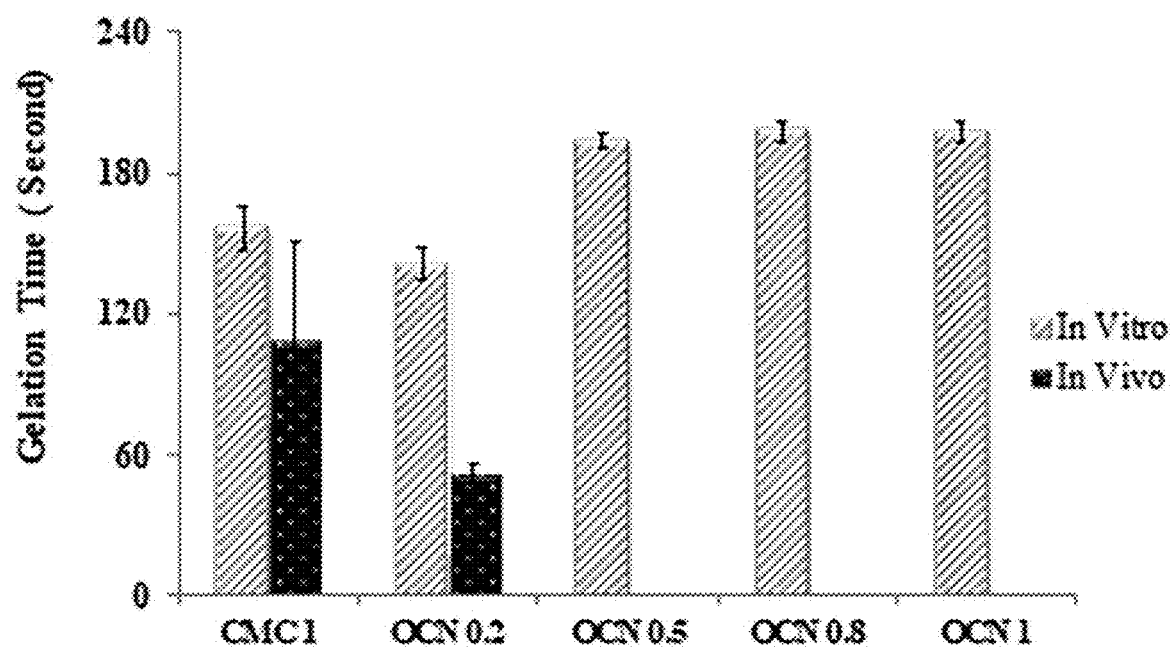
FIG. 8 shows gelation time of hydrogel measured in vitro by test tube inversion method and in vivo injection. In vivo gel formation was significantly faster compared to in vitro gelation. Results are expressed as mean±SD.

FIG. 8 is a graph showing gelation time of hydrogel measured in vitro by the test tube inversion method and in vivo injection and Table 1 is a table showing FIG. 8. In vivo gel formation was significantly faster compared to in vitro gelation. In vitro, the gelation of OCN 0.2 was faster, compared to CMC 1 and OCN with a different composition and, in particular, gelation of OCN 0.2 occurred at 20 seconds and was almost completed within 3 minutes at physiological temperature (FIG. 8).

TABLE 2

| | Sample name | | | | |
|---|---|---|---|---|---|
| | CMC 1 | OCN 0.2 | OCN 0.5 | OCN 0.8 | OCN 1 |
| Approx. In vitro gelation time (sec) | 156 | 141 | 193 | 198 | 197 |
| Approx. In vivo gelation time (sec) | 107 | 51 | | | |

As a result, the hydrogel solutions according to the present invention could be maintained on damaged tissues with an irregular shape after injection and rapidly turned into a non-flowing hydrogel. Therefore, the hydrogel solution has an appropriate gelation time applicable to adhesion prevention.

As mentioned above, the physical OCN 0.2 hydrogel has excellent thermosensitivity and injectability, and appropriate gelation time and temperature, which make it easy to handle and cover the affected tissues unrestrictedly as compared with solid anti-adhesive sheets, particularly, in minimally invasive laparoscopic surgery.

TEST EXAMPLE 7

In Vivo Degradation and Biocompatibility Test of Hydrogel

Figure 9:
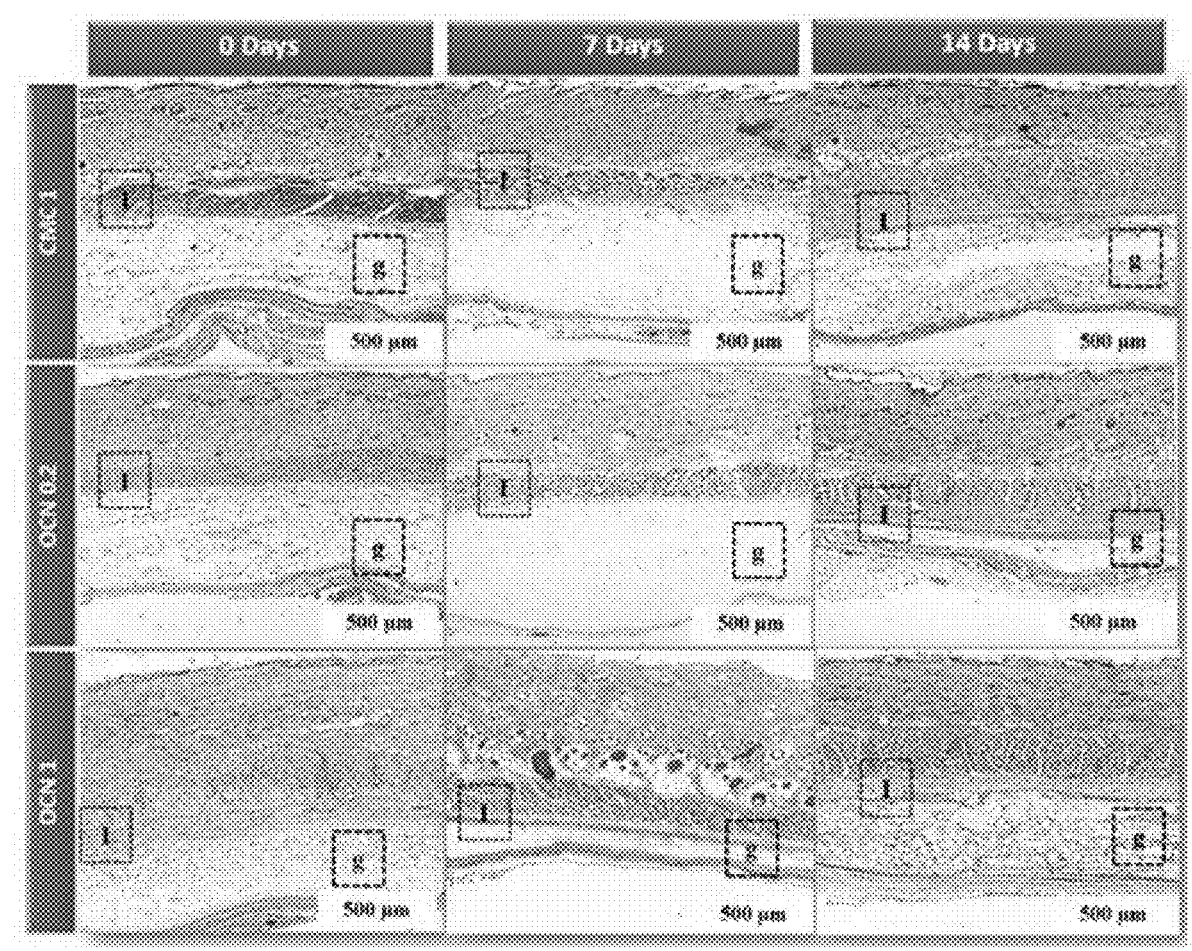
FIG. 9 shows in vivo degradation and biocompatibility of different hydrogels after subcutaneous injection and histological observations of HE-stained slices of tissues surrounding the injection site at different time points. OCN 0.2 shows better degradation over time than other types of gels containing OCN. I=interface between gel and connective tissue, g=gels.

FIG. 9 shows in vivo degradation and biocompatibility of different hydrogels after subcutaneous injection and histological observations of HE-stained slices of tissues surrounding the injection site at different time points. Among the samples, CMC 1 and OCNF 0.2 showed excellent degradation over time without significant migration of more fibroblasts and other inflammatory cells towards the interface between gels and connective tissues, and in gels. On the other hand, the sample OCN 1 exhibited migration of a considerable amount of fibroblasts towards the interface between gel and connective tissues, and in gel.

Accordingly, OCN 0.2 showed better degradation over time than other types of gel containing OCN and thus excellent biocompatibility (I=interface between gel and connective tissue, g=gel).

TEST EXAMPLE 8

In Vivo Anti-Adhesion Efficacy of Hydrogel

Generally, peritoneal adhesions usually occurred within 7 to 10 days after surgery and resulted from a complex cascade regulated by different cellular and humoral factors. On day 4 or 5 after trauma, fibroblasts invaded the fibrinous adhesions, and the initial fibrin-composed matrix was gradually replaced by deposited collagen, leading to the formation of permanent fibrous adhesions. According to the process of adhesion formation, it is very important to block invasion of fibroblasts to prevent peritoneal adhesions. The OCN 0.2 hydrogel showed excellent performance on prevention of rBMSC adhesion, which might be explained by hydrophilicity of the hydrogel surface. CMC is a water soluble polymer so it can diffuse into the culture solution from the gel (FIG. 6).

Figure 10:
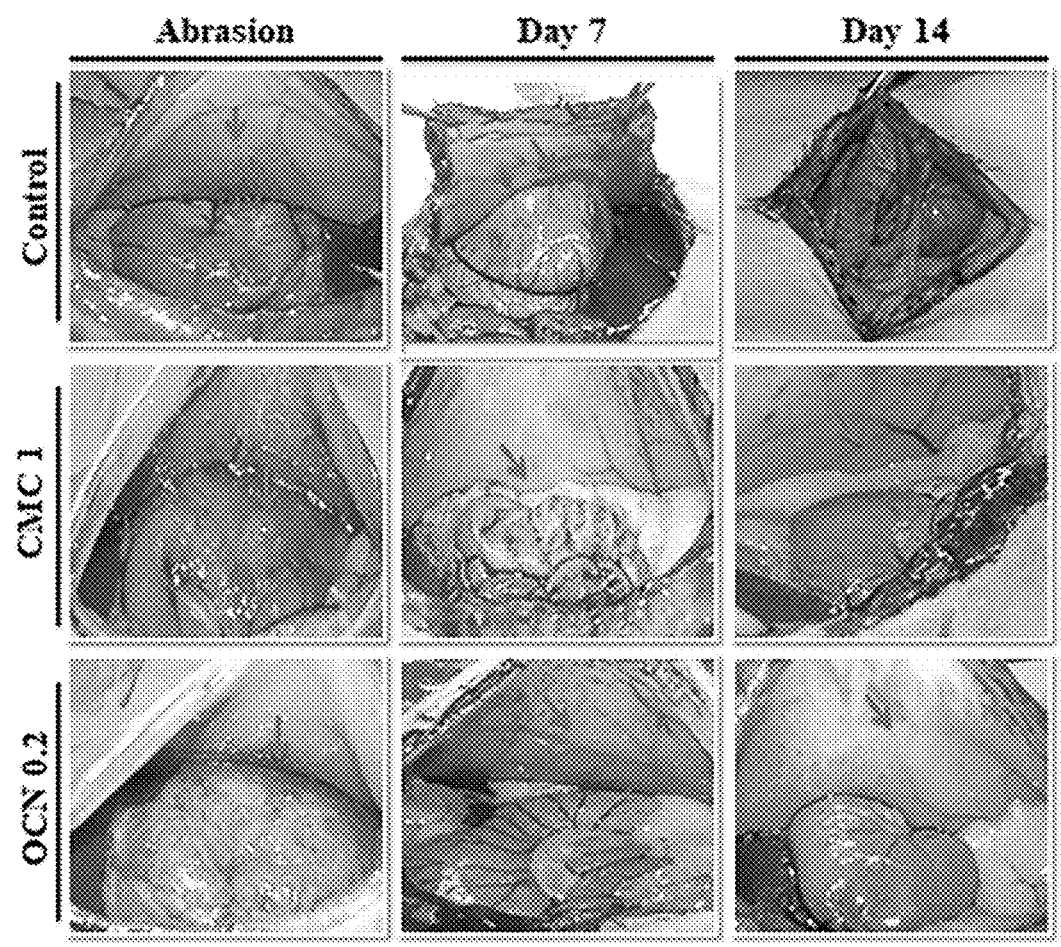
FIG. 10 shows the establishment of sidewall defect-cecum abrasion rat models and the application of hydrogel to defects. Arrows were used to indicate the defect created on the abdominal wall. Adhesions were observed in the control group on day 7 and became severe at day 14 after surgery. No adhesion between the defected wall and abraded cecum was observed in rats treated with hydrogel OCN 0.2 on day 7 and day 14.

FIG. 10 is an image showing the establishment of sidewall defect-cecum abrasion rat models and the application of hydrogel to the defects. Arrows were used to indicate the defect created on the abdominal wall. Adhesions were observed in the control group on day 7 and became severe at day 14 after surgery. No adhesion between the defected wall and the abraded cecum was observed in rats treated with hydrogel OCN 0.2 on day 7 and day 14.

Figure 11:
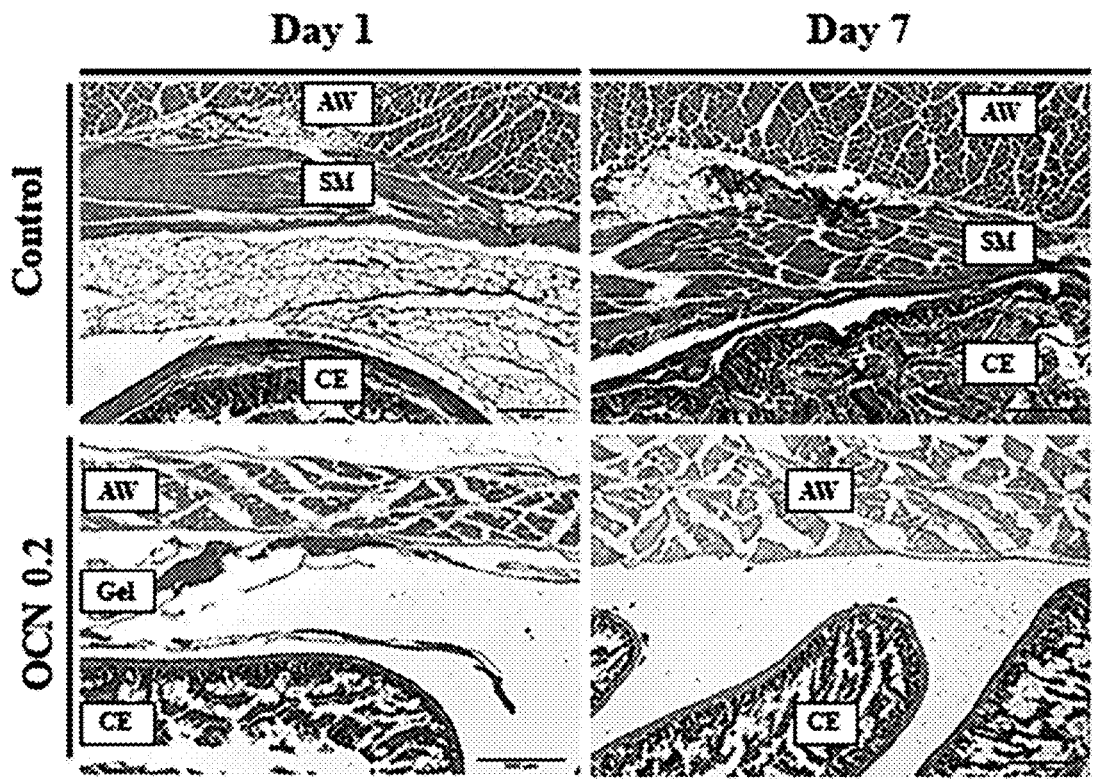
FIG. 11 shows histological examination of peritoneum and ceca wall tissues from rats treated with normal saline (NS), and OCN 0.2 hydrogel on day 7 and day 14. AW=abdominal wall, SM=smooth muscle cells, CE=cecum wall.

FIG. 11 shows histological examination of peritoneum and cecum wall tissues from rats treated with normal saline (NS), and OCN 0.2 hydrogel on day 7 and day 14. AW=abdominal wall, SM=smooth muscle cells, CE=cecum wall. As a result, as compared to control group, rats treated with 0.2 hydrogel did not show smooth muscle cells, which means that adhesion was not formed.

Accordingly, evaluation results of anti-adhesion efficacy of the OCN 0.2 hydrogel on the rat model of sidewall defect-cecum abrasion showed that, as compared to the normal saline group, the adhesion score and adhesion area of the hydrogel group were obviously reduced. In conclusion, the results revealed that the OCN 0.2 hydrogel could more effectively prevent postoperative peritoneal adhesions without side effects and promote the remesothelialization of injured cecum and abdominal wall (FIGS. 10 and 11).

The present invention provides a method for preparing an injectable thermosensitive hydrogel for preventing adhesion including mixing methyl cellulose, polyethylene glycol, oxidized cellulose nanofibers and carboxymethyl cellulose. The injectable thermosensitive hydrogel for preventing adhesion is a sol at a low temperature and induces rapid gelation upon in vivo implantation due to thermosensitivity of in vivo transforming into a gel. In addition, the hydrogen can be rapidly in vivo changed into physical hydrogel without separate additives or chemical reaction. In addition, the injectable thermosensitive hydrogel for preventing adhesion exhibits excellent biodegradability and biocompatibility, has no cytotoxicity, inhibits in vitro migration of rat bone marrow mesenchymal stem cells (rBMSCs), and exhibits anti-adhesion efficacy in a rat model of sidewall defect-cecum abrasion in vivo, thus being useful as an effective anti-adhesive agent.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preparing an injectable thermosensitive hydrogel for preventing adhesion comprising: mixing methyl cellulose, polyethylene glycol, oxidized cellulose nanofibers and carboxymethyl cellulose; adding water to the resulting mixture, followed by heating, to prepare a mix solution; and cooling and stirring the solution to prepare an injectable thermosensitive hydrogel for preventing adhesion, wherein the methyl cellulose, the polyethylene glycol, the oxidized cellulose nanofibers and the carboxymethyl cellulose are mixed in a weight ratio of 2:1:0.2:0.8.

2. The method according to claim 1, wherein the injectable thermosensitive hydrogel shows a sol-gel transition depending on temperature.

3. The method according to claim 1, wherein the injectable thermosensitive hydrogel is gelled in vivo.

4. The method according to claim 1, wherein oxidized cellulose nanofibers are derived from wood.

5. An injectable thermosensitive hydrogel for preventing adhesion prepared by the method according to claim 1.

6. An injectable thermosensitive anti-adhesive agent comprising methyl cellulose, polyethylene glycol, oxidized cellulose nanofibers and carboxymethyl cellulose, wherein the methyl cellulose, the polyethylene glycol, the oxidized cellulose nanofibers and the carboxymethyl cellulose are mixed in a weight ratio of 2:1:0.2:0.8.

* * * * *